US 6,585,672 B1

(12) United States Patent
Crompton

(10) Patent No.: US 6,585,672 B1
(45) Date of Patent: Jul. 1, 2003

(54) ORTHOTIC DEVICE FOR LIMITING ABDUCTION OF THE LEGS WHILE PERMITTING ADDUCTION, ROTATION, EXTENSION AND FLEXION

(75) Inventor: Wiltse P. Crompton, 1402 Bixby Ave. NE., Bemidji, MN (US) 56001

(73) Assignee: Wiltse P. Crompton, Minneapolis, MN (US)

( * ) Notice: Subject to any disclaimer, the term of this patent is extended or adjusted under 35 U.S.C. 154(b) by 0 days.

(21) Appl. No.: 09/890,345

(22) PCT Filed: Jan. 28, 2000

(86) PCT No.: PCT/US00/02159

§ 371 (c)(1),
(2), (4) Date: Jul. 27, 2001

(87) PCT Pub. No.: WO00/44298

PCT Pub. Date: Aug. 3, 2000

Related U.S. Application Data

(60) Provisional application No. 60/118,033, filed on Feb. 1, 1999.

(51) Int. Cl.⁷ .................................................. A61F 5/00
(52) U.S. Cl. ......................... 602/32; 128/869; 128/876; 128/882
(58) Field of Search ................................ 128/869, 876, 128/878, 879, 882; 70/15, 16, 17; 119/760

(56) References Cited

U.S. PATENT DOCUMENTS

| 879,534 A | 2/1908 | Fraser | |
|---|---|---|---|
| 2,093,744 A | 9/1937 | Tuckey | 128/134 |
| 2,245,293 A | 6/1941 | Ogburn | 128/134 |
| 2,650,590 A | 9/1953 | Moore et al. | 128/134 |
| 3,815,589 A | 6/1974 | Bosley | 128/80 |
| 4,173,974 A | 11/1979 | Belliveau | 128/133 |
| 4,203,433 A | 5/1980 | Prahl | 128/80 |
| 4,422,455 A | * 12/1983 | Olsen | 128/876 |
| 5,076,288 A | 12/1991 | Millard et al. | 128/869 |
| 5,518,010 A | * 5/1996 | Dodge | 128/869 |
| 5,558,628 A | 9/1996 | Bzoch | 602/24 |
| 5,718,672 A | 2/1998 | Woodman | 602/23 |

* cited by examiner

Primary Examiner—Michael A. Brown
(74) Attorney, Agent, or Firm—Westman, Champlin & Kelly, P.A.

(57) ABSTRACT

An orthotic device for limiting abduction of the legs of a wearer includes first and second flexible bands (10, 12) for attachment to the legs of the wearer. A fastener (14) slidably fastens the bands together and includes first and second straps (30, 32) each having first and second portions (34, 36, 38, 40) connected to the anterior and posterior aspects of the respective band. The straps form adjustable loops that are slidably connected to a ring (50). The straps are adjustable (42, 44) to adjust the limit of abduction, and the sliding connection of the fastener permits adduction, differential rotation, extension and flexion.

21 Claims, 5 Drawing Sheets

ORTHOTIC DEVICE FOR LIMITING ABDUCTION OF THE LEGS WHILE PERMITTING ADDUCTION, ROTATION, EXTENSION AND FLEXION

CROSS REFERENCE TO RELATED APPLICATIONS

This application claims benefit of PCT Application No. PCT/US00/02159, filed Jan. 28, 2000, and entitled ORTHOTIC DEVICE FOR LIMITING ABDUCTION OF THE LEGS WHILE PERMITTING ADDUCTION, ROTATION, EXTENSION AND FLEXION, which claims priority to U.S. Provisional Application No. 60/118,033, filed Feb. 1, 1999, entitled ADD-A-BANDS.

BACKGROUND OF THE INVENTION

This invention relates to an orthotic device that limits the abduction of the legs while permitting normal adduction, differential rotation, extension and flexion, and particularly to an orthotic device to aid in correcting abduction while encouraging normal development of the hips and developmental movement patterns.

The hip is a ball and socket joint having motion in three axes. Normal development of the hip joint is directly dependent on the proper positioning of the femoral head in the acetabular socket and the motion of the joint in all three axes. One axis of motion of the hip joint is generally referred to as extension and flexion, and is the movement of the leg in a back-to-front orientation; extension being toward the back and flexion being toward the front. The second axis of the hip joint is referred to as abduction and adduction, and is the movement of the leg in the lateral (abduction) and medial (adductioia) directions; moving the legs laterally (abduction) tends to spread the legs whereas moving the legs medially (adduction) causes one leg to approach the other. The third axis is rotation with external rotation being that motion where the anterior portion of the leg rotates laterally (away from the other leg) and internal rotation being that motion where the anterior portion of the leg rotates medially (toward the other leg).

Development of the hip begins in utero and continues over approximately the first eight to nine years of a child's life. With normal growth and development, compressive forces, first from crawling and then from walking, transmit through the hip from the femur to the pelvis generally increasing the depth of the acetabular socket and the formation of the femoral head. This cooperative development continues until normal acetabular depth is reached and the femoral head is formed to approximate a ball. To walk normally, a child must achieve sufficient strength and control to be able to achieve hip extension and flexion while bearing his or her own weight and maintaining a neutral position with regard to the second and third axes (abduction, adduction and rotation). In addition, the child must have good control of rotation.

Leg motion is not well controlled for some children with neuromuscular abnormalities. As a result, their legs may often be in a position of abduction. Consequently, anticipated hip development of the acetabular and femoral head may be affected due to persistent abnormal positioning. Without proper positioning, there is an increased risk that the hip joints may not develop sufficient depth for the needed stability. Stability may also be increased by the strengthening of the muscles around the hip joints when the legs are moving in supportive alignment.

In the past, it has been common to use a strap wrapped around the child's legs to counteract the tendency for abduction of the legs. Such devices did little more than restrain the child, and did not contribute to the development of the hip joint through normal motion and forces through the hip associated with ordinary crawling and walking.

Woodman, in U.S. Pat. No. 5,718,672, proposed a device by which bands were fastened to the legs. An elastic strap interconnects the bands to urge the legs toward each other in adduction and internal rotation. Hence, the elastic interconnecting strap biased the legs to adduction and internal rotation and against abduction and external rotation. However, the Woodman device did not adequately promote extension and flexion of the legs associated with normal walking or crawling. Thus, the Woodman device retained the legs in a more neutral position and restricted extension, flexion and rotation as well as abduction. Children using the Woodman device experienced tugging on one leg as the other moved, such as when crawling or walking. Another difficulty with the Woodman device is that it inhibits differential rotation, namely simultaneous internal rotation of one leg and external rotation of the other leg, as in a twisting motion. Such motion is considered essential in the development of the normal movement patterns.

SUMMARY OF THE INVENTION

The present invention provides an orthotic device having first and second flexible bands each having anterior and posterior aspects relative the legs of the wearer. A fastener slidably fastens the first and second bands and includes first and second straps each having a first portion connected to the anterior aspect of the respective band and a second portion connected to the posterior aspect of the respective band. The straps are slidably connected together.

In a preferred form of the invention, the fastener includes a ring and the first and second straps are arranged as respective first and second loops passing through the ring.

In another preferred form of the invention, an adjustable connector fastens a portion of each flexible strap to the respective flexible band to adjust the size of the respective loop.

In one embodiment, the first and second flexible bands are arranged to be wrapped around the legs of the wearer. A band connector secures the flexible band to the leg. In another embodiment, the first and second flexible bands are integral with pant legs of a garment.

Optionally, tether straps connect a midportion of each flexible band adjacent the band connector to one end portion of the band. Also optionally, other tether straps connect each flexible strap to the respective band adjacent the adjustable connector.

Another aspect of the invention resides in a method of limiting abduction of the legs of a wearer while permitting extension, differential rotation, adduction and flexion of the legs. An orthotic device is provided having first and second flexible members and a fastener slidably fastening the first and second members. The fastener includes first and second straps each having a fir portion connected to the anterior aspect of the respective member and a second portion connected to the posterior aspect of the respective member. The straps are slidably connected together. The first and second members are attached to respective legs of the wearer. The fastener is then adjusted to establish a limit to abduction of the legs. Preferably, the first and second straps are adjustable loops, and the fastener is adjusted by adjusting a size of each loop.

DETAILED DESCRIPTION OF THE ILLUSTRATIVE EMBODIMENTS

Figure 1:
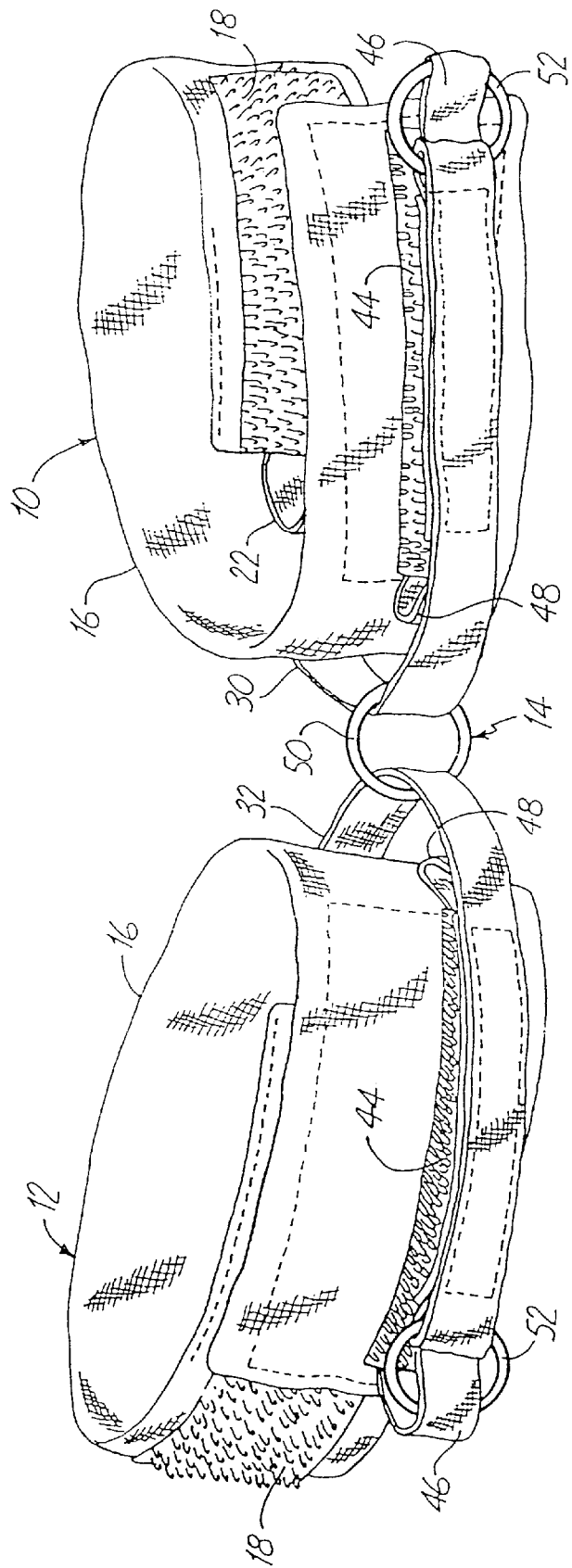
FIG. 1 is a perspective view of an orthotic device according to a first embodiment of the present invention.
Figure 2:
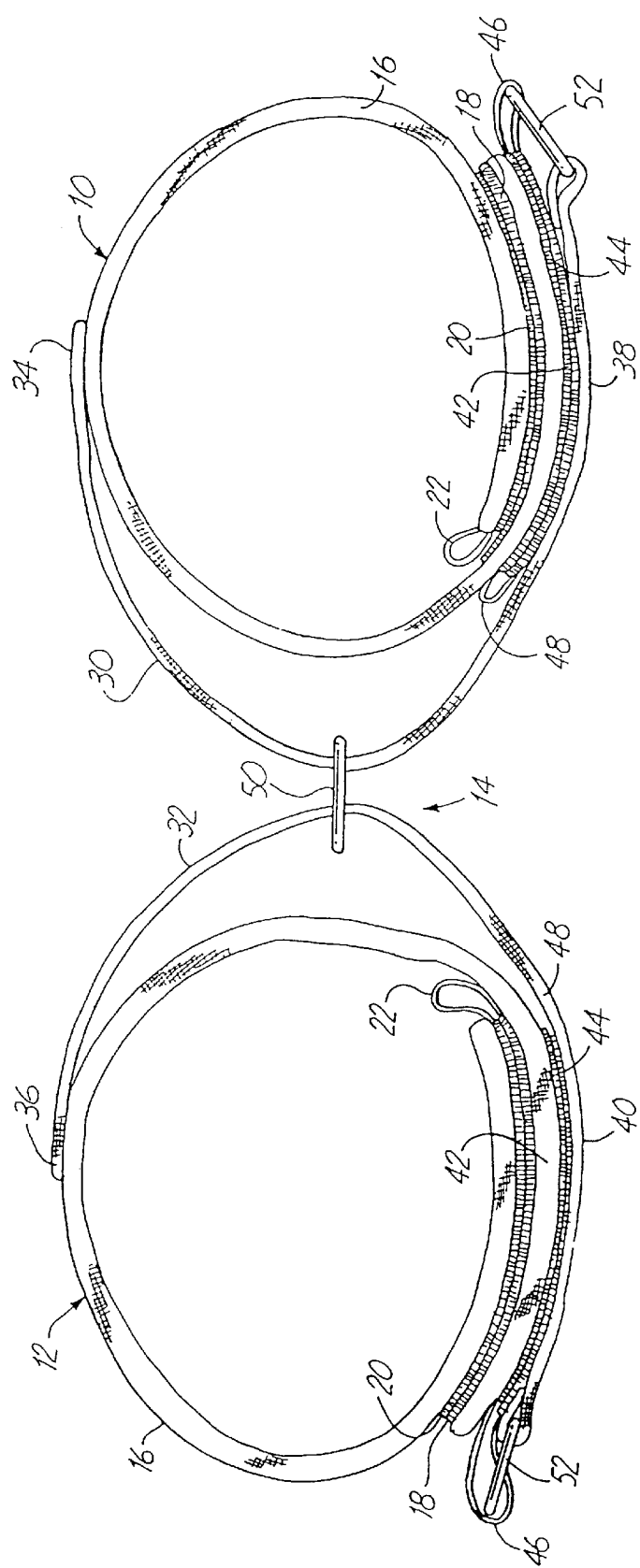
FIG. 2 is a plan view of the embodiment illustrated in FIG. 1.

As illustrated in FIGS. 1 and 2, the orthotic device according to the present invention comprises a right leg band assembly 10, a left leg band assembly 12 and an adjustable sliding fastener 14 connecting band assemblies 10 and 12 together. All references to the right and left band assemblies are in relation to the wearer's right and left. Additionally, although FIG. 1 illustrates primarily the posterior side of the orthotic device, the device may be attached to the wearer oppositely so that FIG. 1 illustrates primarily the anterior side. Each band assembly 10, 12 comprises a flexible band member 16 having a length greater than the circumference of a single leg to which the band is to be attached. The ends of band 16 are arranged to overlap, and a hook and loop fastener fastens the ends together to secure band 16 to the respective leg of the wearer. In a preferred form of the invention, the hook portion 18 of the hook and loop fastener is attached to the outside surface of band 16 at one end thereof, and is arranged to be overlapped by the loop portion 20 of the fastener attached to the inside surface of the opposite end of band 16 at the opposite end thereof. Optionally, a flexible elastic tether strap 22 is connected between the end of strap 16 adjacent fastener portion 18, and to a more central location of strap 16 adjacent to an end of fastener portion 20.

The adjustable sliding fastener 14 includes flexible straps 30 and 32 each attached at one end 34, 36 to the anterior side of band 16. Fasteners 38 and 40 fasten the opposite ends of straps 30 and 32 to the posterior side of bands 16. Fasteners 38 and 40 preferably comprise a hook and loop fastener in which the hook material 42 is attached to the ends of respective straps 30 and 32 and the loop material 44 is attached to the respective ends of the respective strap 16, opposite loop material 20. Optionally, the confronting ends of materials 42 and 44 are connected with flexible elastic tether straps 46 and 48. As shown particularly in FIG. 2, straps 16 are fastened to form loops. The loops or straps 30 and 32 pass through ring 50 so that straps 30 and 32 slide freely through the ring 50.

Bands 16 are preferably constructed of a suitable flexible fabric, such as cotton, synthetic blend or neoprene. Straps 30 and 32 are preferably constructed of a non-elastic fabric, such as cotton or nylon. Tether straps 22, 46 and 48 are preferably constructed of an elastic fabric to stretch along their lengths. Ring 50 is preferably constructed of metal or rigid plastic and may be of any convenient or decorative shape to satisfy the function herein described. Elastic tether straps 22, 46 and 48 are safety features, and do not contribute directly to the operation of the device. It will be appreciated that without those straps, bands 16 and straps 30 and 32 could be unfolded for considerable length that a child could become wrapped in the strap or band. Consequently, as a safety feature, straps 22, 46 and 48 tether bands 16 and straps 30, 32 limit the extension of the bands and straps so they might not be inadvertently misused. If straps 46 and 48 are eliminated, it would be preferred to provide some type of object, such as a decorative ring 52, at the free ends of straps 30 and 32 to prevent inadvertent separation of straps 30 and 32 from ring 50.

Figure 5:
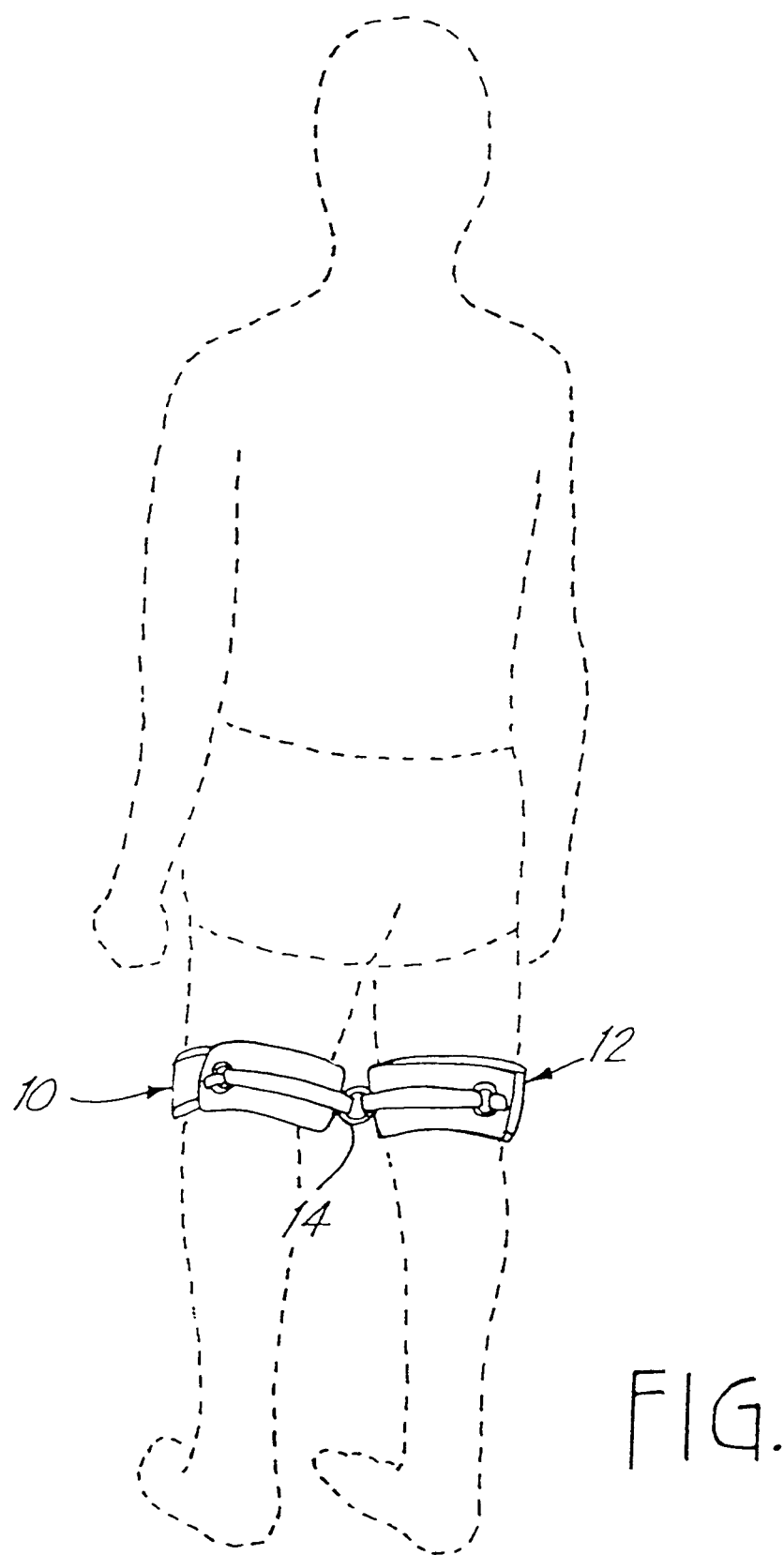
FIG. 5 is a perspective view of the orthotic device on a child.

As shown in FIG. 5, in the use of the orthotic device, bands 16 are fastened to the legs of the wearer immediately above the knees with the adjustable fasteners 38 and 40 preferably to the posterior of the child. Fasteners 30 and 40 are adjusted so that the size of the loops formed by the straps establish a desired limit to the abduction of the legs.

Figure 3:
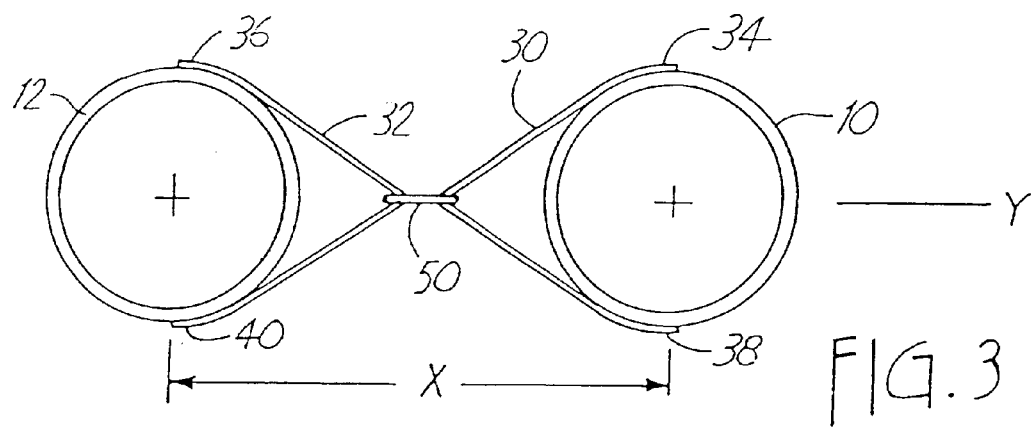
FIGS. 3 and 4 are plan views of an orthotic device according to the present invention illustrating the principles of operation.
Figure 4:
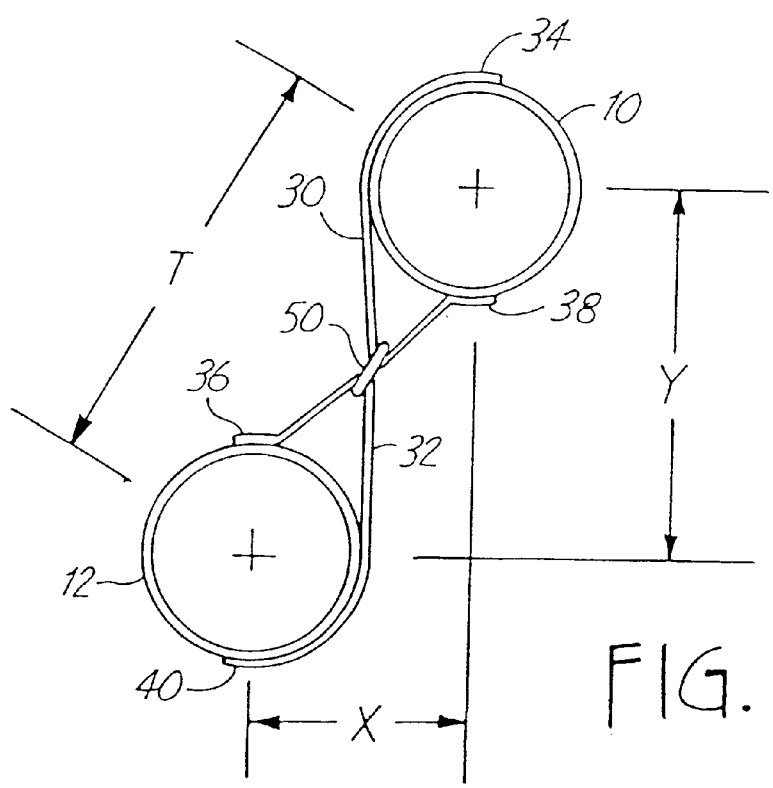

FIGS. 3 and 4 illustrate the operation of the sliding fastener formed by ring 50. FIG. 3 illustrates the position of the legs when the child is standing or lying flat. In this case, each strap 30 and 32 forms a loop, the size of which is established by the position of fastening at 38 and 40. As a result, the loop formed by each strap 30 and 32 is slightly less than half the free length of the strap between the anterior 34 and posterior 38. The maximum abduction of the legs, represented by distance X, is established by the size of the loops. FIG. 4 illustrates extension and flexion of the legs, as may exist when the child is crawling or walking. In this case, the size of the loop formed by each strap 30 and 32 remains approximately the same so that the distance D between the legs remains unchanged. However, ring 50 has slid along the straps so that the portions between ring 50 and the anterior of strap 30 and the posterior of strap 32 have substantially increased, allowing the child to move the legs in flexion and extension by a distance Y. The abduction X is significantly reduced, while the gait during a walking or crawling motion is 2Y. It will be appreciated that the geometry of the orthotic device provides a normal flexion and extension movement, as would be associated with normal crawling or walking, but that abduction is limited.

It is common for children with low muscle tone and lax hip ligaments to move from a sitting position to a prone position on their stomachs by bending forward at their hips as they spread their legs in extreme abduction. Both legs rotate internally and move backwardly until the prone position is reached. During this time, stiffness is maintained at the knees during movement with a lack of differentiation in the legs. With the orthotic device according to the present invention, the abduction of the legs of the child is restrained and limited by the size of the loops formed by straps 30 and 32. The restraint imposed by the straps, and the sliding connection between the straps provided by ring 50, allow the child to move to the side, rather than forward, with the knees bending in response as one thigh rotates internally and the other rotates externally. Thus the child moves into the prone position using pelvic and trunk rotation in a manner similar to children without abnormal muscle tone. Hence, the orthotic device of the present invention permits differential rotation of one thigh rotating externally while the other rotates internally, consistent with normal rotational movements.

When crawling, children with neuromuscular abnormalities often can not assume the normal four-point crawling position with the knees under the hips. Instead, the legs abduct to the sides leaving the child resting on the pelvis. With the orthotic device according to the present invention, abduction is limited and the child is able to pull the knees into position, slightly wider than the hips, in a more normal four-point position. Moreover, the sliding fastener formed by the sliding connection of ring 50 and straps 30 and 32, permits extension and flexion of the legs to allow the child to crawl in a normal manner.

The orthotic device of the present invention is also beneficial to premature infants who generally do not display physiologic flexor tone typical of full-term infants. Pre-term infants tend to have low muscle tone resulting in abduction and extension at the hips. The orthotic device of the present invention assists in promoting a posture more similar to a full-term infant by positioning the legs with decreased abduction and increased flexion to permit development of increased muscle tone and, ultimately, more typical developmental movement patterns.

Figure 6:
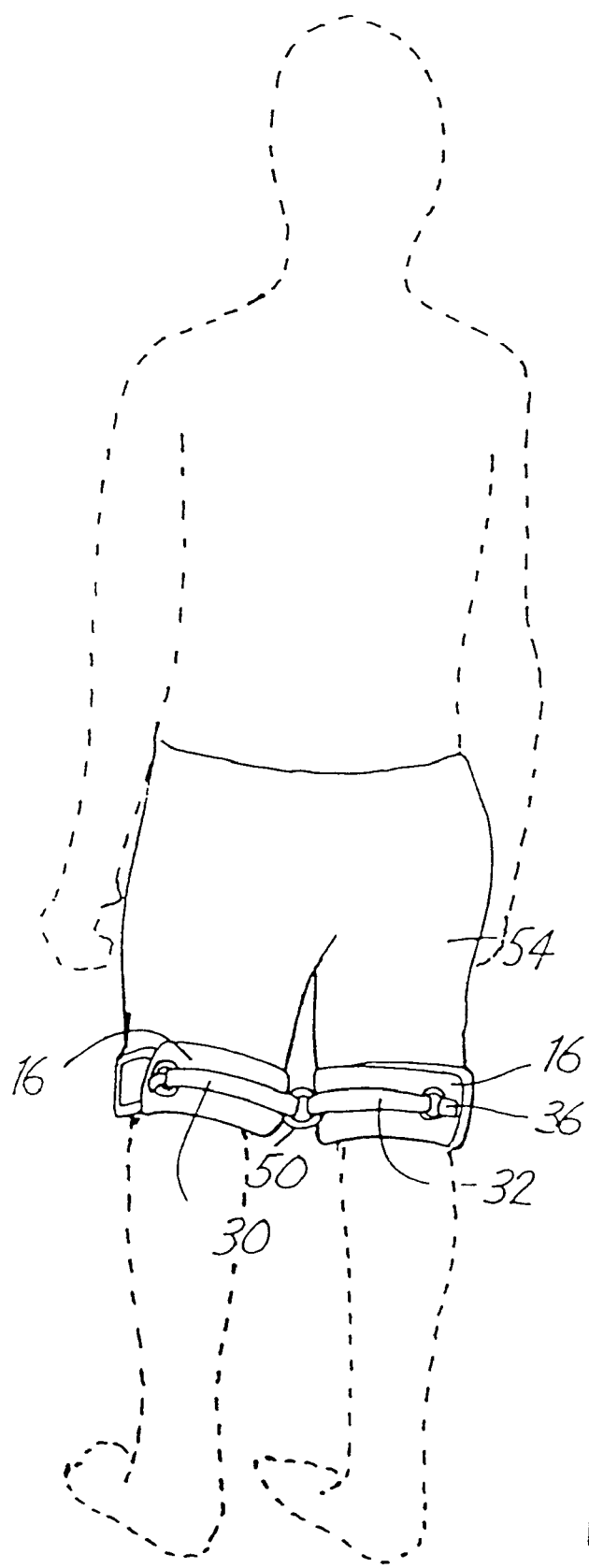
FIG. 6 is a perspective view of an orthotic device according to a second embodiment of the present invention on a child.

FIG. 6 illustrates a second embodiment of the present invention in which the orthotic device is formed as part of a pair of pants or shorts 54 to be worn by the child. In this case, the leg bands may be part of the pant legs, with straps 30 and 32 fastening the bands together as previously described. As in the case of the embodiment illustrated in FIGS. 1, 2 and 5, straps 30 and 36 are fastened together with sliding ring 50. In this case, it is preferred that at least one of the fastening locations 34, 36, 38 and 40 be detachable to allow at least one of the rings and one of the straps 30, 32 to be removed from ring 50. In this manner, at least one of the straps may be separated from the ring so that the child may be dressed in an oversuit, such as a snowsuit or the like.

The embodiment illustrated in FIG. 6 may be further modified by fastening straps 30 and 32 directly to the posterior and anterior of the legs of the garment (permanently and/or with fasteners, as described) so that the pant legs of the garment perform the function of the flexible members or bands 16 to fasten straps 30 and 32 to the legs. This modification eliminates bands 16 altogether, yet retains the sliding fastener between the bands to permit rotation, flexion and extension. However, rotation of the garment about the legs may make adjustment of the limit of abduction more difficult, and render tile orthotic device somewhat less effective.

Other modifications would be readily apparent to those skilled in the art. For example, other types of fasteners, such as buttons or snaps, could be used in place of the hook and loop fasteners. Use of silent fasteners, such as buttons or snaps, may be particularly attractive for use with infants likely to be frightened by the noise of operating loop and hook fasteners. Additionally, while straps 30 and 32 are described as permanently attached to the anterior of the bands or garment, fasteners may be used at both the anterior and posterior locations so that the straps may be adjustable, or even removable, thereby adding to the convenience of attachment and permitting additional control over rotation. Also, while the orthotic device has been described as employing a physical ring for the sliding fastener, it is evident that the loops formed by straps 30, 32 could simply be interconnected in a sliding fashion. Doing so, however, may necessitate the use of a fabric that is smooth so that straps 30 and 32 freely permit movement.

The present invention thus provides an orthotic device capable of improving neutral positioning of the legs in disabled persons, and facilitates the mobility required for ambulation. Moreover, because the device improves the alignment of the femoral head within the acetabular socket, it is believed use of the device will contribute to the improved hip growth and formation. Preliminary tests indicate that children with abnormal neuromuscular development learn efficient developmental movement patterns in as short as a few hours using the device. Thus, at least for a short time, some children tended to continue use correct movement patterns of their legs after removal of the orthotic device.

The orthotic device of the present invention maintains the legs in improved alignment by limiting excessive abduction displayed by children with low muscle tone and/or laxity in the hip joints. By providing proper alignment, the device provides stability around the hip joints so that the child is capable of remaining in a normal position without collapsing. Consequently, the child is less likely to maintain a position by locking joints. With the device, a child with low muscle tone and/or laxity in the hip joints may independently move the legs and pelvis in a coordinated manner, encouraging shifting of weight, rotational movement and the development of righting and equilibrium reactions. Thus, the device encourages the child to discover movement patterns inherent within the nervous, muscular and skeletal systems consistent with normal efficient movement, and muscles are strengthened as a greater variety of movements are discovered and repeated.

Although the present invention has been described with reference to preferred embodiments, workers skilled in the art will recognize that changes may be made in form and detail without departing from the spirit and scope of the invention.

What is claimed is:

1. An orthotic device for limiting abduction while permitting adduction, extension, flexion, internal rotation and external rotation, of a wearer's legs, the device comprising
   first and second flexible members for attaching to respective legs of the wearer; and
   a fastener slidably fastening the first and second members together, the fastener being so sized and arranged with respect to the first and second flexible members as to limit abduction of the wearer's legs to which the first and second members are attached and to permit independent extension, flexion, internal rotation and external rotation of the wearer's legs to permit normal movement patterns of the legs.

2. The orthotic device of claim 1, wherein the fastener comprises
   first and second flexible straps attached to respective ones of the first and second members, the straps being slidably coupled together and of such length to permit extension, flexion, internal rotation and external rotation of the first and second members.

3. The orthotic device of claim 2, wherein the first and second straps are arranged as respective first and second loops, the straps being slidably coupled together.

4. The orthotic device of claim 3, including a ring, the first and second straps extending through the ring so that each strap is independently slidably attached to the ring.

5. The orthotic device of claim 2, wherein a length of at least one of the straps is adjustable to adjust the limit of abduction of the first and second members.

6. The orthotic device of claim 2, wherein each of the first and second members has anterior and posterior aspects suitably positionable in relation to an anterior and a posterior aspect of the respective leg of the wearer, each of the first and second flexible straps having a first portion connected to the anterior aspect of the respective member and a second portion connected to the posterior aspect of the respective member so that a length of the respective strap forms a respective loop.

7. The orthotic device of claim 6, further including an adjustable connector for fastening one of the first and second portions of each flexible strap to the respective member, the adjustable connector adjusting a length of the respective flexible strap between the first and second portions to thereby adjust the size of the respective loop independently of the member, the loops formed by the respective flexible straps being slidably coupled together.

8. The orthotic device of claim 7, including a ring, the first and second flexible straps extending through the ring so that each flexible strap is independently slidably attached to the ring.

9. The orthotic device of claim 7, including a first tether strap connecting the first flexible strap to the first member adjacent the adjustable connector of the first flexible strap, and a second tether strap connecting the second flexible strap to the second member adjacent the adjustable connector of the second flexible strap.

10. The orthotic device of claim 1, wherein the first member comprises
   a first flexible band arranged to be wrapped around a first leg of the wearer, and
   a first band connector for fastening portions of the first flexible band together to secure the first flexible band to the first leg, and
the second member comprises
   a second flexible band arranged to be wrapped around a second leg of the wearer, and
   a second band connector for fastening portions of the second flexible band together to secure the second flexible band to the second leg.

11. The orthotic device of claim 10, wherein the first and second band connectors adjustably secure end portions of the respective bands together, the device further including a third tether strap connecting a midportion of the first band adjacent the first band connector to one end portion of the first band, and a fourth tether strap connecting a midportion of the second band adjacent the second band connector to one end portion of the second band.

12. The orthotic device of claim 10, wherein the fastener comprises
   first and second flexible straps attached to respective ones of the first and second bands, the straps being slidably coupled together to permit extension and flexion of the first and second bands.

13. The orthotic device of claim 12, wherein each of the first and second bands has anterior and posterior aspects suitably positionable in relation to an anterior and a posterior aspect of the respective leg of the wearer, each of the first and second flexible straps having a first portion connected to the anterior aspect of the respective band and a second portion connected to the posterior aspect of the respective band so that a length of the respective strap forms a respective loop.

14. The orthotic device of claim 13, further including an adjustable connector for fastening one of the first and second portions of each flexible strap to the respective band, the adjustable connector adjusting a length of the respective flexible strap between the first and second portions to thereby adjust the size of the respective loop independently of the member, the loops formed by the respective flexible straps being slidably coupled together.

15. The orthotic device of claim 14, including a ring, the first and second flexible straps extending through the ring so that each flexible strap is independently slidably attached to the ring.

16. The orthotic device of claim 14, including a first tether strap connecting the first flexible strap to the first band adjacent the adjustable connector of the first flexible strap, and a second tether strap connecting the second flexible strap to the second band adjacent the adjustable connector of the second flexible strap.

17. An orthotic device for limiting abduction while permitting adduction, extension, flexion, internal rotation and external rotation, of a wearer's legs, the device having first and second flexible members each having anterior and posterior aspects suitably positionable in relation to an anterior and posterior aspect of a respective leg of a wearer; and first and second straps each having a first portion connected to the anterior aspect of a respective first or second member and a second portion connected to the posterior aspect of the respective first or second member, the straps being slidably coupled together and so sized and arranged with respect to the first and second flexible members as to limit abduction of the wearer's legs to which the first and second members are attached and to permit independent extension, flexion, internal rotation and external rotation of the wearer's legs to permit normal movement patterns of the legs.

18. The orthotic device of claim 17, further including a ring, and the first and second straps are arranged as respective first and second loops with the first and second loops extending through the ring so that each of the first and second straps is independently slidably attached to the ring.

19. The orthotic device of claim 18, including an adjustable connector for fastening a portion of each flexible strap to the respective flexible member to adjust the size of the respective loop independently of the member.

20. A method of limiting abduction of the legs of a wearer while permitting adduction, extension, flexion, internal rotation and external rotation of the legs, the method comprising the steps of:
   providing an orthotic device having
      first and second flexible members each having anterior and posterior aspects suitably positionable in relation to an anterior and posterior aspect of a respective leg of the wearer, and
      a fastener slidably fastening the first and second members, the fastener including first and second straps each having a first portion connected to the anterior aspect of the respective member and a second portion connected to the posterior aspect of the respective member, the straps being slidably coupled together and so sized and arranged with respect to the first and second flexible members as to limit abduction of the wearer's legs to which the first and second members are attached and to permit independent extension, flexion, internal rotation and external rotation of the wearer's legs to permit normal movement patterns of the legs;
   attaching first and second members of the orthotic device to respective legs of the wearer; and
   adjusting the fastener to establish a limit to abduction of the legs.

21. An orthotic device for limiting abduction, while permitting adduction, extension, flexion, internal rotation and external rotation, of a wearer's legs, the device comprising
   first and second flexible members for attaching to respective legs of the wearer;
   first and second flexible straps attached to respective ones of the first and second members, the straps being slidably coupled together and so sized and arranged with respect to the first and second flexible member as to limit abduction of the wearer's legs to which the first and second members are attached while permitting independent extension, flexion, internal rotation and external rotation of the wearer's legs to permit normal movement patterns of the legs; and
   an adjusting member for adjusting a length of at least one of the straps independently of the members to adjust the limit of abduction of the first and second members.

* * * * *